(12) United States Patent
Fuenfschilling et al.

(10) Patent No.: US 7,148,346 B2
(45) Date of Patent: Dec. 12, 2006

(54) PURIFICATION PROCESS

(75) Inventors: Peter Fuenfschilling, Allschwil (CH); Berthold Schenkel, Basel (CH)

(73) Assignee: Novartis AG, Basel (CH)

( * ) Notice: Subject to any disclaimer, the term of this patent is extended or adjusted under 35 U.S.C. 154(b) by 112 days.

(21) Appl. No.: 10/625,142

(22) Filed: Jul. 23, 2003

(65) Prior Publication Data

US 2005/0072736 A1 Apr. 7, 2005

Related U.S. Application Data

(60) Division of application No. 10/021,117, filed on Oct. 29, 2001, now Pat. No. 6,620,325, which is a continuation of application No. 09/652,295, filed on Aug. 31, 2000, now abandoned, which is a continuation of application No. 09/271,672, filed on Mar. 18, 1999, now abandoned, which is a continuation of application No. 08/926,722, filed on Sep. 10, 1997, now abandoned.

(30) Foreign Application Priority Data

Sep. 11, 1996 (GB) ................. 9618952.7

(51) Int. Cl.
*C07D 498/18* (2006.01)
(52) U.S. Cl. .................................... 540/456
(58) Field of Classification Search ................. 540/456
See application file for complete search history.

(56) References Cited

U.S. PATENT DOCUMENTS

| | | | |
|---|---|---|---|
| 3,244,592 A | 4/1966 | Aral | 167/65 |
| 3,503,950 A | 3/1970 | Li | 260/112 |
| 3,527,750 A | 9/1970 | Karr | |
| 3,573,275 A | 3/1971 | Maehr et al. | |
| 3,671,647 A | 6/1972 | Argoudelis et al. | 260/210 R |
| 3,743,633 A | 7/1973 | Goerlich et al. | 260/210.5 |
| 3,804,594 A | 4/1974 | Orjans et al. | 23/270.5 |
| 4,016,258 A | 4/1977 | Said et al. | 424/177 |
| 4,081,354 A | 3/1978 | Christman | |
| 4,203,956 A | 5/1980 | Schrodter et al. | 423/321 |
| 4,271,128 A | 6/1981 | Schrodter et al. | 422/189 |
| 4,328,214 A | 5/1982 | Rink et al. | 424/177 |
| 4,753,734 A | 6/1988 | Ito | 210/657 |
| 4,803,016 A * | 2/1989 | Binderman et al. | 260/403 |
| 4,913,814 A | 4/1990 | Singh et al. | 210/512.2 |
| 4,954,260 A | 9/1990 | Ludmer et al. | 210/634 |
| 5,256,547 A | 10/1993 | Rudat et al. | 435/71.1 |
| 5,359,060 A * | 10/1994 | Hauske | 540/456 |
| 5,382,655 A | 1/1995 | Szanya et al. | 530/317 |
| 5,591,438 A | 1/1997 | Olson et al. | 424/195.1 |
| 5,595,661 A * | 1/1997 | Li et al. | 210/634 |
| 5,616,595 A * | 4/1997 | Chu et al. | 514/344 |
| 5,665,772 A * | 9/1997 | Cottens et al. | 514/514 |
| 5,709,797 A | 1/1998 | Bocchiola | 210/635 |
| 6,706,727 B1 * | 3/2004 | Fleissner et al. | 514/291 |

FOREIGN PATENT DOCUMENTS

| | | |
|---|---|---|
| CA | 2108655 | 4/1995 |
| CH | 633 826 | 12/1982 |
| CH | 0637123 A5 | 7/1983 |
| DE | 295 871 | 11/1991 |
| DE | 295 872 | 11/1991 |
| DE | 295 873 | 11/1991 |
| DE | 298 276 | 2/1992 |
| DE | 298 427 | 2/1992 |
| EP | 427680 A1 * | 5/1991 |
| EP | 652 219 A1 * | 11/1993 |
| EP | 652 219 A1 | 11/1993 |
| EP | 641 861 | 3/1995 |
| EP | 652219 A1 * | 5/1995 |
| GB | 1 223 902 | 3/1971 |
| GB | 1 223 903 | 3/1971 |
| GB | 1257866 | 12/1971 |
| GB | 1 356 056 | 6/1974 |
| GB | 1 521 457 | 8/1978 |
| GB | 2 215 631 | 9/1989 |
| WO | WO 95/06059 | 3/1995 |
| WO | WO 95/11295 | 4/1995 |
| WO | 95/32726 A1 * | 12/1995 |
| WO | 96/12031 A1 * | 4/1996 |

OTHER PUBLICATIONS

Wang-Fan, W.; Kusters, E.; Lohse, O.; Mark, C.-P.; Wang, Y., Journal of Chromatography, A (1999), 864(1), 69-76.*
No Author, "Wikipedia, the free encyclopedia" [online]. Wikimedia Foundation Inc. St. Petersburg, FL, Feb. 6, 2006, [retrieved on Mar. 2, 2006]. Retrieved from the Internet <http://en.wikipedia.org/w/index.php?title=Ascomycin&printable=yes>.*
Prochazka, et al., Chem. Engineer. Science, vol. 31, pp. 179-186 (1976).
Lo and Baird, Encyc of Chem. Tech., 4th ed., vol. 10, pp. 125-180, J. Wiley & Sons, 1979.
Vogel, Text book of Practical Organic Chem., Longman, 4th Edition, 1978, (pp. 211,217, 219, 220) from Experimental Techniques.

* cited by examiner

*Primary Examiner*—Bruck Kifle
(74) *Attorney, Agent, or Firm*—Thomas R. Savitsky

(57) ABSTRACT

This invention provides a process for purifying a cyclosporin, e.g. cyclosporin A, or a macrolide, to a high degree of purity on a large scale. In another aspect this invention provides a bulk quantity of cyclosporin A with an impurity level of less than about 0.7%, e.g. about 0.5%, and compositions thereof.

3 Claims, 5 Drawing Sheets

PURIFICATION PROCESS

Figure 1:
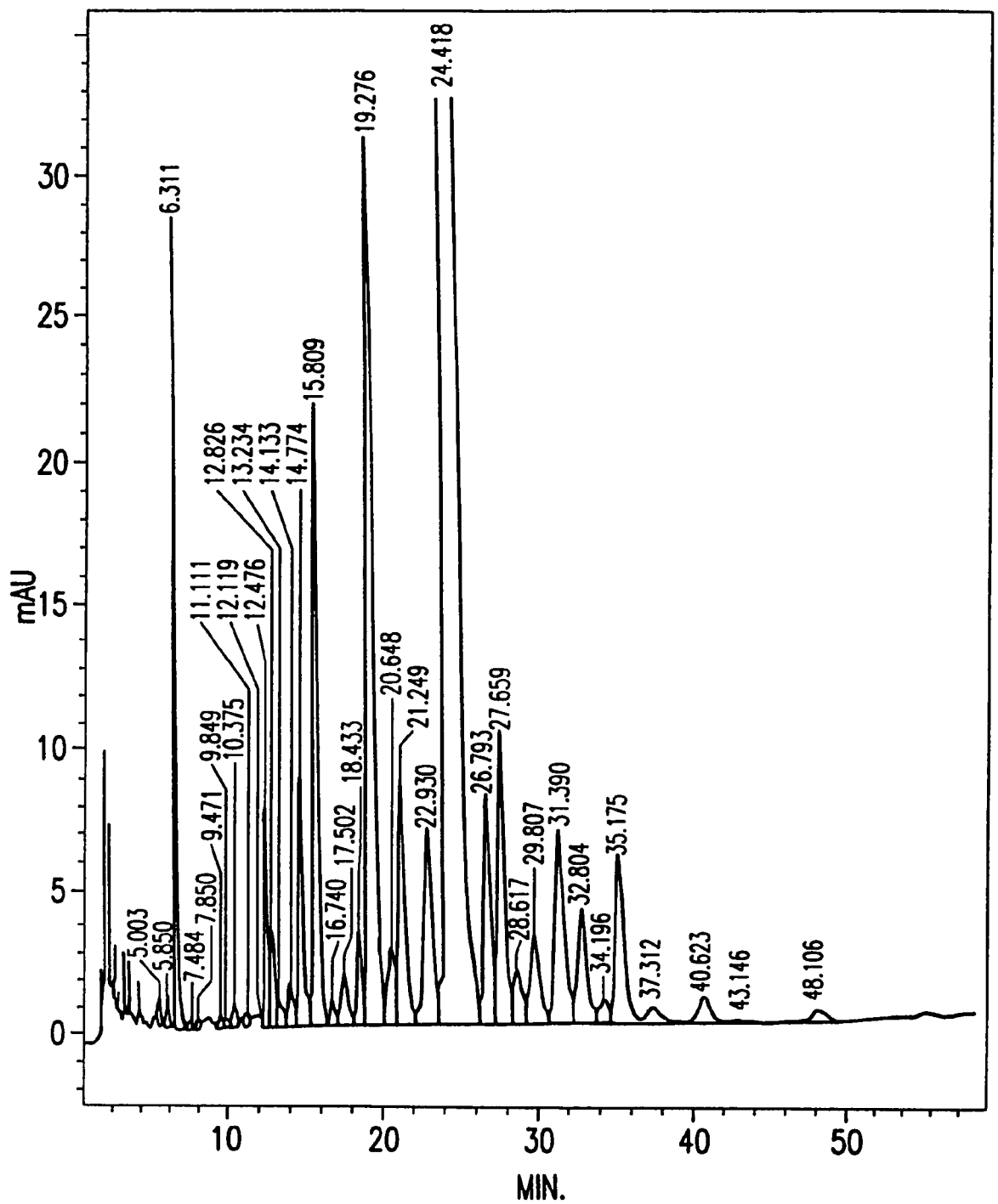

This is a divisional of application Ser. No. 10/021,117, Oct. 29, 2001 now U.S. Pat. No. 6,620,325, which is a continuation of application Ser. No. 09/652,295, Aug. 31, 2000, abandoned, which is a continuation of application Ser. No. 09/271,672, Mar. 18, 1999, abandoned, which is a continuation of application Ser. No. 08/926,722, Sep. 10, 1997, abandoned.

The present invention relates to a purification process, and in particular to a process for purifying a product from impurities having relatively close distribution coefficients one with another.

Extraction processes are well-known for separating hydrocarbons in the petrochemical industry. It is known that distribution coefficients of the hydrocarbons between given phase systems in such applications differ substantially one from another.

Reviews of extraction methods are published, for example, in Kirk-Othmer Encyclopedia of Chemical Technology, 4th edition, Vol. 10, p. 125–180, pub. John Wiley & Sons 1993, and in The Handbook of Solvent Extraction, ed. Lo, Baird & Hanson, pub. Krieger 1991. The contents of these publications are incorporated herein by reference.

Presently large-scale purification of products of biotechnological processes is generally carried out by extraction or adsorption chromatography. Such products include peptides, macrolides and proteins which are generally produced as mixtures of products having closely-related structural and/or physical properties. Fractional extraction processes known in the petrochemical industry have hitherto not been applied in the biotechnology industry on a large scale for purification of active agents, e.g. peptides, having closely-related physical properties one with another. The present applicants consider a major problem to be that the respective distribution coefficients of biotechnological products and impurities between given phases are close one with another.

Accordingly, in one aspect, the present invention provides a process for purifying a product from a feedstock containing one or more impurities having closely-related physical properties to the product, which process comprises feeding the feedstock into an extraction column under conditions adapted for separating more- or less-polar impurities from the feedstock, wherein a lighter phase flows counter to a heavier phase, thereby forming an output in one phase containing the product containing less more- or less-polar impurities so that the output contains the product in a substantially purified form.

The feedstock for the above process may be provided by output from a chromatographic purification or other pre-purification step, e.g. decantation. This process may be conducted such that the output serves as input for a subsequent chromatographic purification, e.g. in a series arrangement.

In another aspect, this invention provides a process for purifying a product from a feedstock containing one or more impurities having closely-related physical properties to the product, which process comprises a) feeding the feedstock into a first extraction column under conditions adapted for separating more- or less-polar impurities from the feedstock, wherein a lighter phase flows counter to a heavier phase, thereby forming a first output in one phase containing the product containing less more- or less-polar impurities, and b) feeding the first output into a second extraction column under conditions adapted for separating less- or more-polar impurities respectively from the first output, wherein the lighter phase flows counter to the heavier phase, thereby forming in one phase a second output, so that the second output contains the product in a substantially purified form.

The feedstock may be prepared by known methods, for example by fermentation. When the product is produced in a fermentation broth, the broth may be filtered and mixed with a solvent from which the product may be precipitated in an impure state, e.g. containing about 15% to about 30% by weight impurities. Typically the fermentation broth may undergo several cleaning and work-up steps prior to use as feedstock in the process of this invention. Initial filtration(s) and precipitation(s) serve to remove, for example, natural dyes and easily separable impurities from the product, and may serve to enhance phase separation in the extraction steps.

As used herein, the term "phase" is understood to mean a system having at least one component. The phase may comprise a single solvent or a mixture of, for example 2, 3 or more solvents.

As used herein, the term "closely-related physical properties" is understood to mean that the product is difficult to separate from the one or more impurities. The closely-related physical properties may include, for example, the respective distribution coefficients of the product and one or more impurities between two phases. For a cyclopeptide, e.g. a cyclosporin, and in particular cyclosporin A, ratios of distribution coefficients, i.e. distribution coefficient of cyclosporin A/distribution coefficient of impurity, may be between about 3 and about 0.4, e.g. between about 1.5 and about 0.8. These ratios are known as selectivities.

As used herein, the term "large scale" as applied to purification plant, is understood to mean a plant having an output of about one or more tonnes of purified product per annum, e.g. 10 tonnes per annum, or more e.g. around 20 to around 40 tonnes.

As used herein, the term "impurity" is understood to mean an undesirable component.

The process of this invention may be applied to a wide variety of products, e.g. peptides, such as cyclosporins, for example Cyclosporin A and derivatives thereof, Cyclosporin D and derivatives thereof, or Cyclosporin G and derivatives thereof. An example of a Cyclosporin D derivative is, for example ([3'-desoxy-3'-oxo-MeBmt]$^1$-[Val]$^2$-Ciclosporin) as disclosed in EP 296122; or macrolides, for example rapamycins and derivatives thereof, and ascomycins and derivatives thereof, produced for example by fermentation. Examples of macrolides which may be purified using the process of this invention include rapamycin; 40-O-(2-hydroxy)ethyl rapamycin as described in PCT/EP93/02604; ascomycin; 33-epi-chloro-33-desoxyascomycin as described in EP 427680 in Example 66a; ascomycin derivatives disclosed e.g. in EP 569337 and in EP 626385, for example 5,6-dehydro-ascomycin as disclosed in EP 626385; or an ascomycin derivative known as FK506.

A method for producing Cyclosporin A is disclosed, for example, in Example 1 of British patent specification 1,491,509. Methods of preparing FK506 are described in EP 184162.

A variety of columns are known and available commercially. In one embodiment of this invention, a single column is used which is a countercurrent column adapted for mechanical agitation and/or stirring of the feedstock/phase system. In another embodiment of this invention, two or more columns are used, at least one of which is a countercurrent column adapted for mechanical agitation and/or stirring of the feedstock/phase system.

Preferably the column(s) includes mechanical agitation, e.g. rotary agitation or reciprocating plate. An extraction column adapted for mechanical agitation is available commercially from the Kuehni company, Switzerland.

In another aspect, this invention provides a countercurrent liquid-liquid extraction column adapted for rotary agitation having a sufficient number of trays or compartments to effect, in use, separation of a pharmaceutical from impurities.

In a further aspect, this invention provides the use of a countercurrent liquid-liquid extraction column adapted for rotary agitation for separating a pharmaceutical from impurities.

The column(s) may be adapted for temperature adjustment of the phases. A jacket may be provided, for example, to maintain a desired temperature within the column. When purifying, for example a cyclosporin, temperatures may be maintained within each column at between about 0 and about 100° C., preferably between about 20 and about 80° C., and more preferably between about 30 and about 60° C.

It may be advantageous to conduct the process using a first column in series arrangement with a second and a third column, wherein the second column is in parallel arrangement with the third column. The Applicants contemplate such a configuration when, for example, the plant is to be situated in a building having a covering of limited height.

The phases chosen for the extraction step(s) of the process may depend on the distribution coefficient between phases, and solubility of the product in each phase under consideration. Fast and efficient separation of the phases is desirable, and separation may be substantially complete, for example within about one minute, preferably 30 seconds, more preferably within about 20 seconds.

A two-phase system is used in the process of this invention, wherein the phases are immiscible or substantially immiscible one with another. At least one phase may be an aqueous phase. The two-phase system separates to form a lighter, e.g. non-aqueous organic, phase comprising at least one solvent component, and a heavier, e.g. aqueous, phase comprising at least one solvent component and water. The product to be purified may be more readily soluble in one phase component which, therefore, serves as extracting component.

Preferably one phase is an aqueous phase and one phase is a non-aqueous phase. The aqueous phase may contain at least about 20%, e.g. more than about 40% by weight water, and may contain up to 100% by weight water. The aqueous phase may be the heavier phase.

The phase systems used in the processes of this invention may comprise, as organic phase, at least one hydrocarbon, e.g. a $C_5$ to $C_{12}$ alkane, e.g. n-heptane, cyclohexane or methylcyclohexane. As aqueous phase, the present applicants contemplate, in addition to water, ketones, e.g. acetone; esters, e.g. amyl acetate, n-butyl acetate or isopropyl acetate; or alcohols, e.g. methanol, ethanol, propanol, isopropanol, n-butanol, s-butanol, t-butanol or a pentanol. Acetone is a preferred extracting solvent for cyclosporin A.

It will be appreciated that at least one component is common to both phases. The common component may comprise any of the above-mentioned solvents, e.g. water; hydrocarbons; alcohols; ketones; or esters.

The present applicants have found an n-heptane/acetone/water system to be effective for purifying acomycin and derivatives thereof, rapamycin and derivatives thereof and cyclosporin A. In one embodiment, the following phase system is used to purify cyclosporin A: the lighter phase comprises a mixture in weight-% of about 75% n-heptane and about 25% acetone; the heavier phase comprises a mixture of about 50% acetone and about 50% water. The water content of the lighter, substantially non-aqueous phase is typically less than 10% by weight, preferably less than about 2% by weight based on the total weight of the non-aqueous phase.

In another embodiment, the following phase system is used to purify 40-O-(2-hydroxy)ethyl rapamycin: the lighter phase may comprise a mixture in weight-% of about 75%, e.g. 74%, n-heptane, about 25%, e.g. 25.5% acetone and a small quantity of water, e.g. 0.5% water. The heavier phase may comprise a mixture of a small amount e.g. 0.4% n-heptane, about 50%, e.g. 52.8%, acetone and about 50%, e.g. 46.8%, water.

The present applicants have found an n-heptane/isopropanol/water system to be effective for purifying 33-epi-chloro-33-desoxyascomycin. In one embodiment, the following phase system is used to purify 33-epi-chloro-33-desoxyascomycin: the lighter phase comprises a mixture in weight-% of about 90% n-heptane, e.g. 89%, and about 10% isopropanol, e.g. 11%; the heavier phase comprises a mixture of about 32% isopropanol, e.g. 31%, and about 68% water, e.g. 69%.

The distribution coefficient is defined herein as the ratio of the concentration (in g/unit volume) of product in the lighter phase to the concentration (in g/unit volume) of product in the heavier aqueous phase at 40° C. The following distribution coefficients are obtained for cyclosporins between 75% n-heptane / 25% acetone as lighter organic phase, and 50% acetone/50% water as heavier aqueous phase:

| Cyclosporin | Distribution coefficient (to one decimal place) |
| --- | --- |
| A | 0.8 |
| B | 0.4 |
| C | 0.3 |
| D | 1.7 |
| Dihydro-A | 1.0 |
| G | 1.3 |
| L | 0.5 |
| U | 0.6 |

From the above, it will be apparent that the respective distribution coefficients for cyclosporins are relatively close one with another. When purifying Cyclosporin A, for example, the impurities to be separated from Cyclosporin A typically include other cyclosporins.

One advantage of this process is that Cyclosporin A may be prepared substantially free from impurities such as other Cyclosporins, e.g. Cyclosporin B, Cyclosporin C, or dihydro-Cyclosporin A. Thus the respective amounts of cyclosporin derivative impurities, e.g.

Cyclosporin B, Cyclosporin C and Cyclosporin G in Cyclosporin A purified using the process of this invention, are typically at or below analytically detectable limits using HPLC. Thus the impurities in cyclosporin A are found to amount to less than about 0.7% by area using HPLC, e.g. about 0.5% or less, e.g. about 0.3%.

In another aspect, therefore, this invention provides a bulk quantity, i.e. 1 kg or more, e.g. 10 kg or more, e.g. 20, 30, 40, 50 kg or more cyclosporin A with an impurity level of less than about 0.7%, e.g. 0.5% or less, by area using HPLC. This invention further provides a bulk quantity of cyclosporin A having a purity level of 99.5% or greater, e.g. 99.7% or greater. The impurities found in purified cyclosporin A of this invention consist of other cyclosporins.

In another aspect this invention provides a composition comprising cyclosporin A as active agent in a bulk purified form, wherein the amount of impurities present is below 0.7%, e.g. 0.5% by area using HPLC.

The composition may be orally administrable and may be an emulsion, microemulsion, a microemulsion preconcentrate or a solid dispersion. The composition may comprise components disclosed for example in published UK patent application GB 2 222 770, the contents of which are incorporated herein by reference.

Distribution coefficients for 40-O-(2-hydroxy)ethyl rapamycin are found to lie between 0.7 and 1.4 when using n-heptane/acetone/water phases. Ratios of distribution coefficients, i.e. selectivities, for rapamycin to 40-O-(2-hydroxy)ethyl rapamycin typically range from about 1.4 to about 2.3, e.g. around 1.5.

The distribution coefficient for 33-epi-chloro-33-desoxyascomycin is found to be around 7.6 using the above n-heptane/isopropanol/water phase system. The selectivity of ascomycin derivative side product to 33-epi-chloro-33-desoxyascomycin is found to be approximately 1.44.

The pH of the aqueous phase, when present, is typically between about 2 and about 9, for example pH 7.

The extraction process conditions, including the number of theoretical stages, may be selected using routine experimentation and, for example, computer simulation. A program suitable for such a purpose is available commercially under the trade name ASPEN PLUS.

Exact conditions for working this invention typically depend on a number of factors, including the dimensions of the column(s), fluid dynamics, stirrer speed, efficiency and number of trays or compartments.

Compartments having an efficiency of about 10 to 30%, e.g. 12 to 25%, may be suitable for the column(s) of this invention. Column efficiency, as used herein, is understood to mean the number of actual stages divided by the number of theoretical stages.

It will be appreciated by those skilled in this art that an extraction column, in use, may exhibit a flooding point. The respective flow rates of the phases may therefore be chosen to maintain the system in the or each column at below the flooding point, for example around 10 or 20% below the flooding point. In this way, high turbulence and fast mass transfer between phases may be obtained.

The present applicants have found that for a given column, the flooding point may be reached when a particular stirrer speed is reached and/or exceeded, hereinafter referred to as the critical speed. Stirrer speeds applied in a column in the process of this invention may be between about 15 and about 200 rpm. On a large scale, typical stirrer speeds may be between about 5 and about 60 rpm. The applicants have obtained good results using a stirrer speed about 10 to 20% below the critical speed.

In one embodiment of this invention, the same solvent system(s) may be used in each column, and the respective flow rates may be varied so that the desired product may be extracted into either phase. The respective flow rates may be determined using routine experimentation and computer simulation using, for example, the above-mentioned computer program.

The processes of this invention may result in a highly pure product, in particular when combined, for example, with distillation, precipitation and/or crystallisation steps. After a crystallisation step, solvent(s) may be distilled off, collected and recycled. The product may be obtained in known solid form.

The process of this invention may be applied to the purification of, for example, cyclosporins to achieve purity greater than 98.5%, e.g. 99.3% or greater by area using HPLC, and improved overall yield compared to chromatographic purification.

The order of extraction used in the two-step process of this invention may be reversed: the less polar impurities may be removed from the impure product in the first column, and the more polar impurities removed in the second column. If the product to be purified is to be separated from a single impurity, or only from less polar components, or only from more polar components, the process may be adapted to include a single extraction step, for example, only above step a) or only step b).

Following is a description by way of example only and illustrated by accompanying drawings, of a purification process of this invention conducted in a pilot plant having an output capacity of about 1 kg/day purified product, and on a commercial scale having an output capacity of at least about 10 kg/day purified product.

FIGS. 1 to 4 each show a chromatograph of Cyclosporin A and impurities at stages of the purification process.

Figure 5:
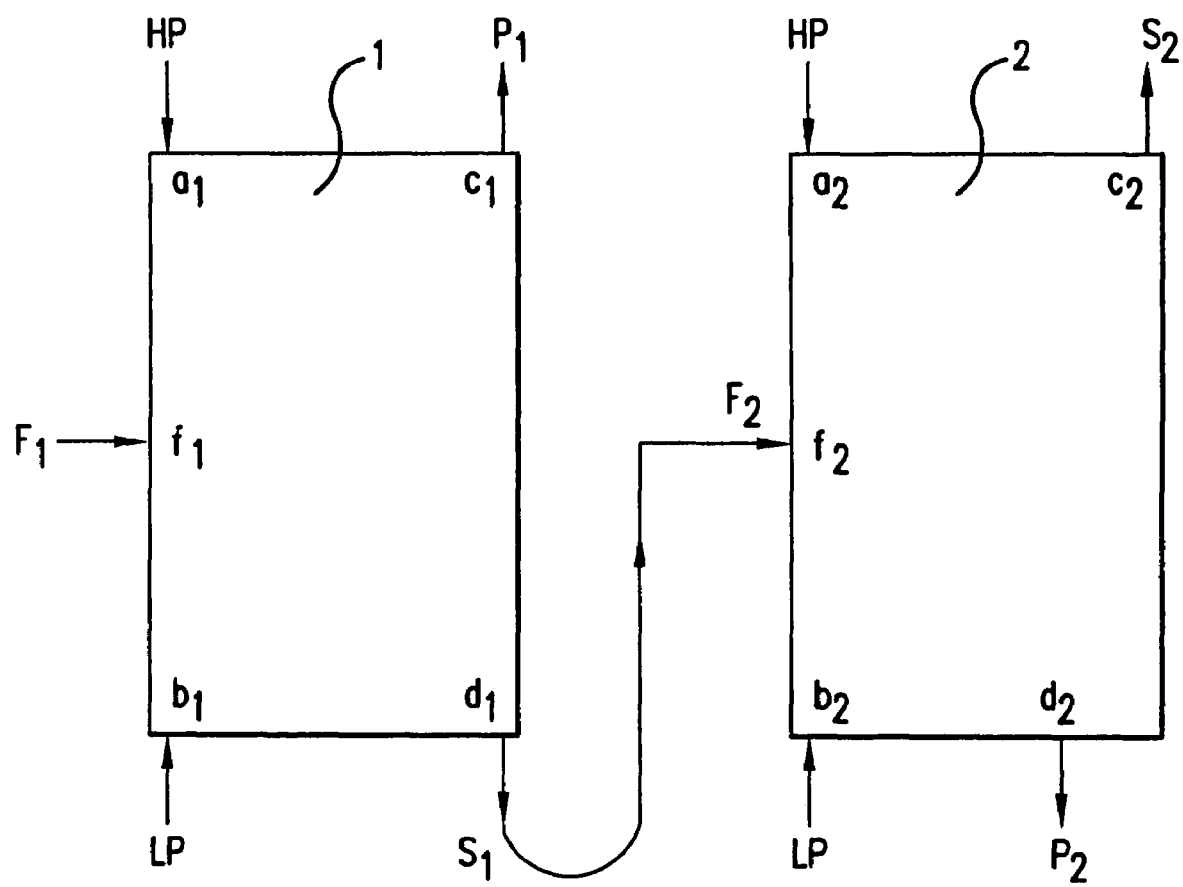

FIG. 5 is a schematic representation of phase flows.

Cyclosporin A is produced in a fermentation broth which is worked up and filtered. FIG. 1 shows a chromatograph of the filtered product containing Cyclosporin A; Cyclosporin A is represented by the peak at 24.418.

Pilot Plant Scale

The filtered product is mixed with acetone, and Cyclosporin A is partially crystallised from the acetone to form a feedstock F1. Feedstock F1 is fed into a first extraction column (1, pilot scale) half way up the column at a central zone f1. Column 1 is fitted with mechanical agitation. A lighter (organic) phase LP, consisting of 25 wt-% acetone and 75 wt-% n-heptane, is fed into column 1 at a lower zone b1. A heavier (aqueous) phase HP, consisting of 50% water and 50% acetone, is fed into column 1 at an upper zone a1. The following flow rates are used in the first column:

|  | liters/hour |
| --- | --- |
| Feed (F1) | 4.2 |
| heavier (aqueous) phase (HP) | 12.7 |
| lighter phase (LP) | 13 |

Figure 2:
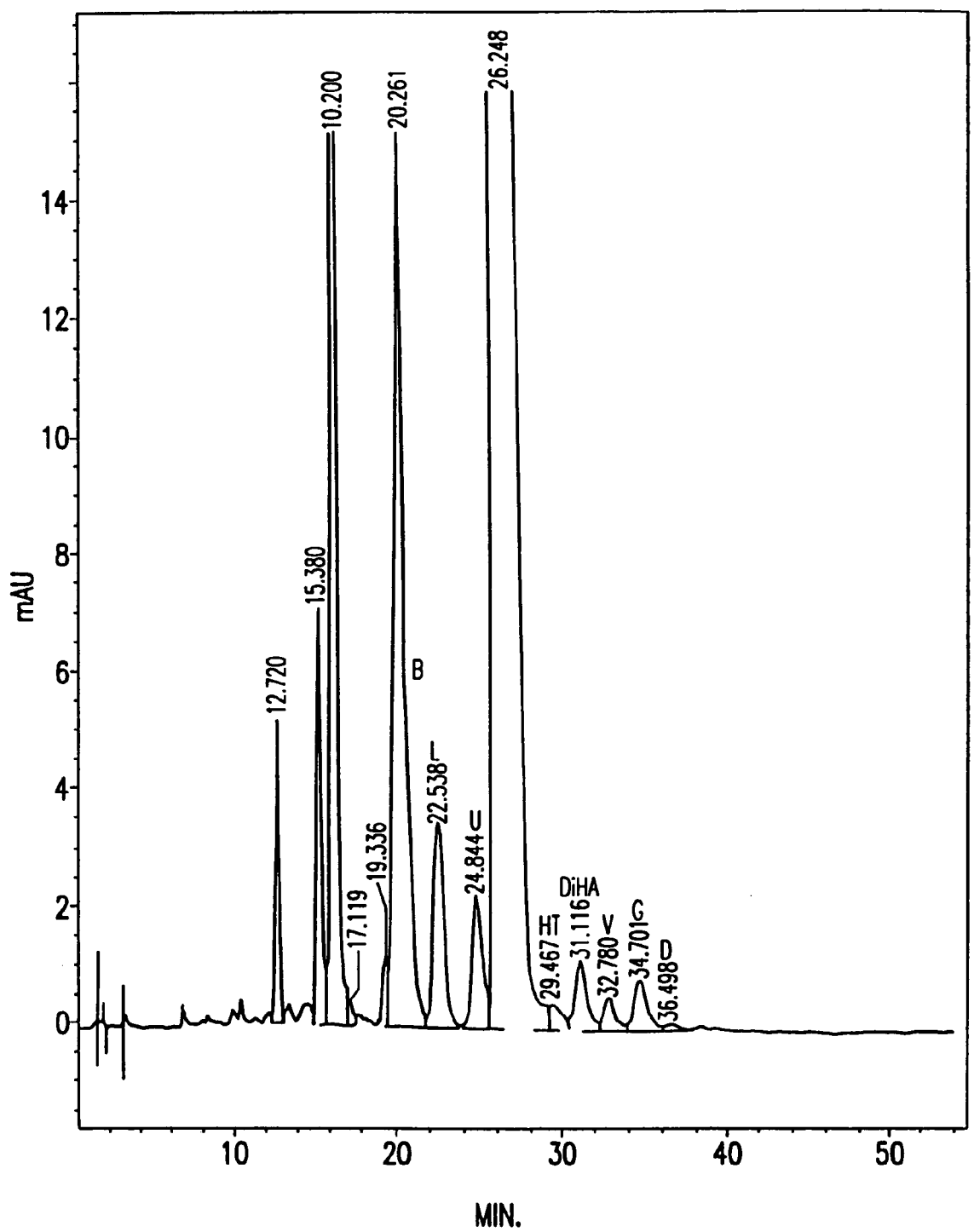

A product stream S1 containing Cyclosporin A with more polar impurities, exits from the lower zone in the aqueous phase at d1; less polar impurities are removed in the lighter phase P1 which exits from column 1 at upper zone c1. FIG. 2 shows a chromatograph of the stream S1 at this stage; Cyclosporin A is represented by the peak at 26.248.

Figure 3:
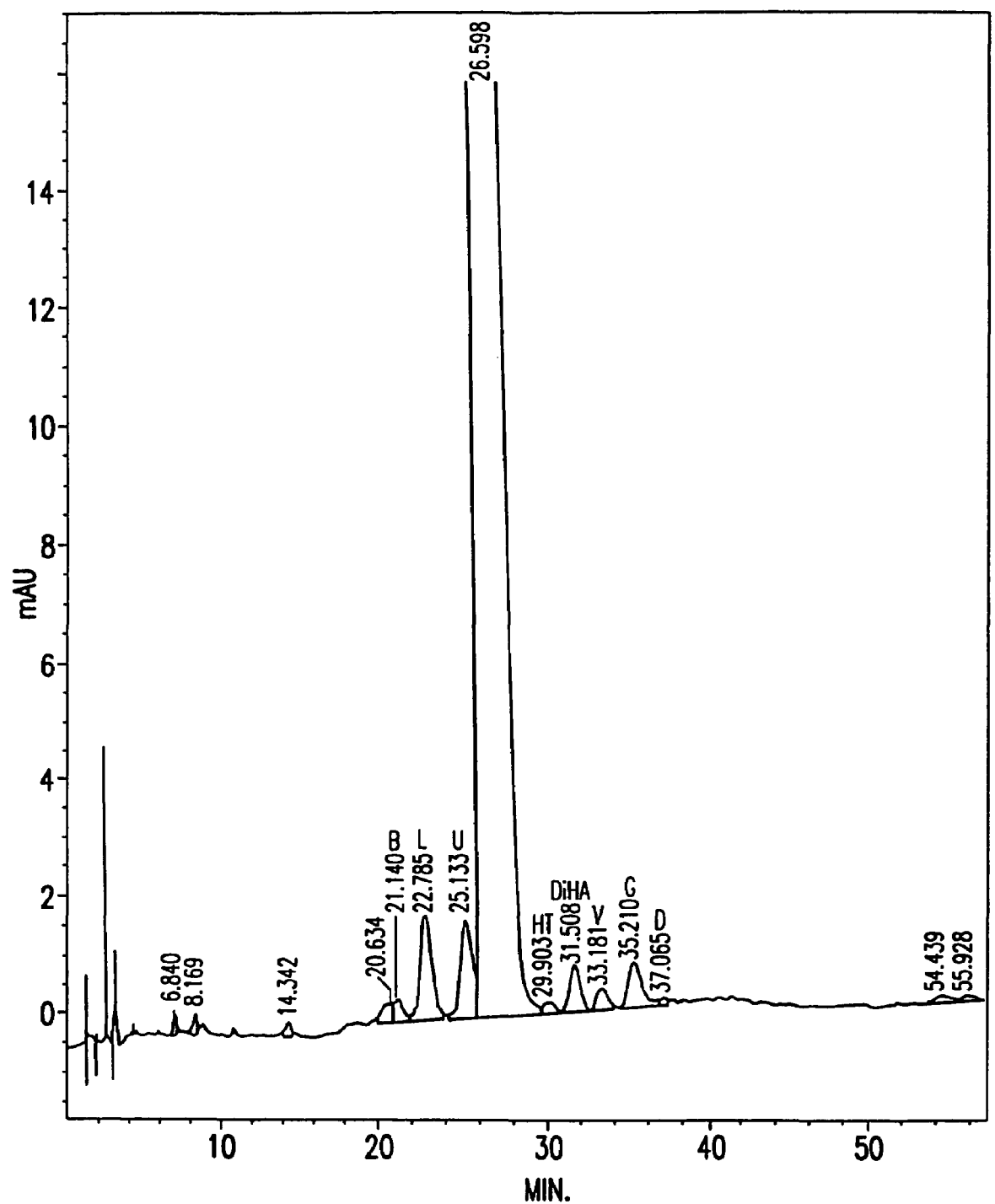

Product stream S1 serves as feedstock F2 for a second column (2, pilot scale), and is fed into column 2 halfway up column 2 at central zone f2. The second column is also fitted with mechanical agitation. The lighter phase LP is fed into column 2 at a lower zone b2, and heavier (aqueous) phase HP is fed into column 2 at upper zone a2. More polar impurities are removed in the heavier phase P2 which exits from column 2 at lower zone d2. Cyclosporin A is removed in product stream S2 with lighter phase from column 2 at upper zone c2. FIG. 3 is a chromatograph of the stream S2 mixture at this stage; Cyclosporin A is represented by the peak at 26.598.

Arrowheads in FIG. 5 indicate directions of phase/product stream flows with respect to the columns.

The following flow rates are used in the second column:

|  | liters/hour |
| --- | --- |
| Feed (F2) | 3.1 |
| heavier (aqueous) phase (HP) | 9.7 |
| lighter phase (LP) | 17.7 |

Figure 4:
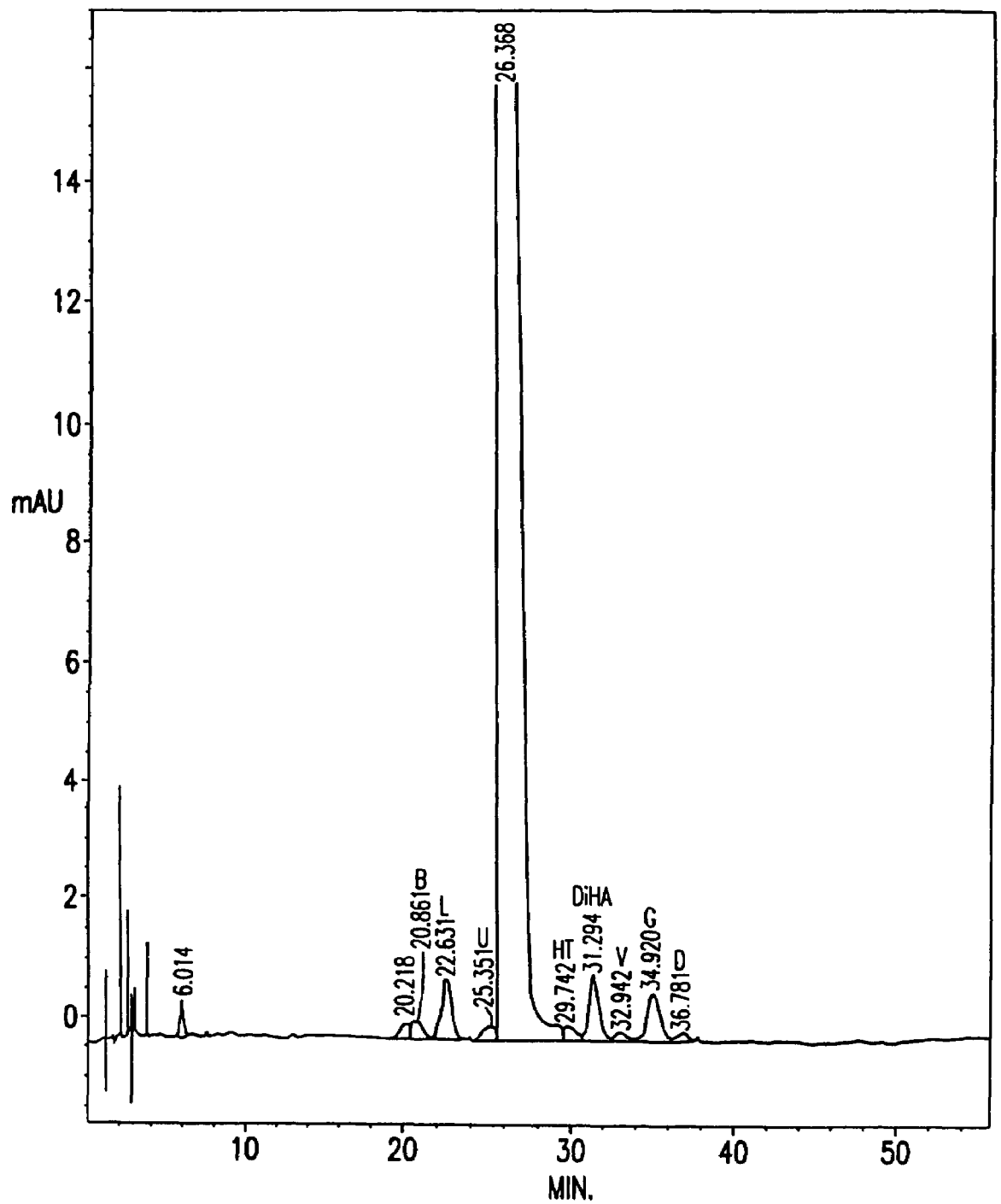

Organic solvents are distilled from the Cyclosporin A/lighter phase mixture which is subsequently mixed with acetone, from which Cyclosporin A is crystallised. Cyclosporin A at a purity of >98.5% is obtained, as determined by high-performance liquid chromatography. FIG. 4 shows a chromatograph with purified Cyclosporin A represented by the peak at 26.368.

The internal diameter of each column employed in the pilot plant is 6 cm.

Commercial Scale

A. For large, commercial, scale operation, using similar geometric parameters and hydrodynamic conditions to those used in the pilot plant, the Applicants calculate that 40 theoretical stages are required; the first column has an overall 25% efficiency and 160 compartments. The first column has a height of about 25 m and an internal diameter of about 30 cm. For the second column, the Applicants calculate that 30 theoretical stages are required, and 120 compartments. The second column is calculated to have a height of about 25 m and an internal diameter of about 80 cm.

A purification plant is constructed using the above parameters with the two columns in series arrangement.

A bulk quantity of 50 kg cyclosporin A is produced. On analysis of the cyclosporin using HPLC, impurities amount to less than 0.5% by area. This implies a purity of at least 99.5% by weight.

B. Using similar geometries and hydrodynamic conditions to those used in the pilot extraction column, the Applicants calculate that 44 theoretical stages at an efficiency of approximately 27% are required in the first CCE step. The first column is calculated to have a height of approximately 27 m, an internal diameter of approximately 45 cm and 160 compartments. For the second column, the Applicants calculate that 62 theoretical stages at an efficiency of approximately 38% are required. The second column is calculated to have a height of about 34 m and an internal diameter of about 70 cm, and 160 compartments.

A purification plant is constructed using these parameters. A third column is provided substantially identical in construction and dimensions with the second column. The first column is in series arrangement with the second and third columns. The second and third columns are in mutually parallel arrangement. Output from the first column is divided and fed into the second and third columns.

A bulk quantity of 100 kg cyclosporin A is produced. On analysis of the cyclosporin using HPLC, impurities amount to less than 0.5% by area. This suggests a cyclosporin A purity of at least 99.5% by weight.

The present invention provides a continuous process for purifying on a large scale a product(s) from impurities, which product(s) and impurities have similar physical properties one with another. Greater purities at a particular yield, or greater yields at a particular purity, may be achieved using this process than by using chromatographic purification. The process is more economical in operation since product streams do not have to be divided and/or recycled as is generally required with absorption chromatography.

The countercurrent process of this invention is surprisingly more efficient than purification by chromatography, and multiple recycling steps are avoided. The process of this invention allows simulation and adjustment of process parameters more readily in order to achieve a desired purity than when using chromatography. Compounds of closely-related structure are surprisingly more easily separated one from another on a commercial scale, e.g. Cyclosporin A from Cyclosporins B and C.

The invention claimed is:

1. A process for purifying on a large scale a product from a feedstock containing one or more impurities having closely-related physical properties to the product, which process compromises:

feeding the feedstock into an extraction column under conditions adapted for separating more-or-less polar impurities from the feedstock, wherein a lighter phase flows counter to a heavier phase, thereby forming an output in one phase containing the product containing less more- or less-polar impurities so that the output contains the product in a substantially purified form, wherein the lighter phase compromises heptane and acetone or heptane and isopropanol, the heavier phase compromises water and acetone or water and isopropanol, and the product is rapamycin or 40-O-(2-hydroxy)ethyl rapamycin or ascomycin or a derivative thereof selected from the group consisting of 33-epi-chloro-33-desoxyascomycin, 5,6-dehydro-ascomycin or FK506.

2. A process of claim 1, wherein the lighter phase comprises about 25 wt-% n-heptane and about 75 wt-% acetone, or about 90 wt-% n-heptane and about 10 wt-% isopropanol.

3. A process of claim 1, wherein the heavier phase comprises about 50 wt-% water and about 50 wt-% acetone, or about 68 wt-% water and about 32 wt-% isopropanol.

* * * * *